US006933318B1

(12) United States Patent
Kassebaum et al.

(10) Patent No.: US 6,933,318 B1
(45) Date of Patent: Aug. 23, 2005

(54) TOPICAL ORGANIC ECTOPARASITICIDAL FORMULATIONS

(75) Inventors: James Web Kassebaum, Indianapolis, IN (US); Paul Thomas Pugh, Knightstown, IN (US); William Webster Thompson, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 213 days.

(21) Appl. No.: 10/048,242

(22) PCT Filed: Jul. 26, 2000

(86) PCT No.: PCT/US00/19549

§ 371 (c)(1),
(2), (4) Date: Sep. 13, 2002

(87) PCT Pub. No.: WO01/12156

PCT Pub. Date: Feb. 22, 2001

Related U.S. Application Data

(60) Provisional application No. 60/148,508, filed on Aug. 12, 1999.

(51) Int. Cl.⁷ ..................... A01N 43/02; A61K 31/335
(52) U.S. Cl. ...................................................... 514/450
(58) Field of Search ................................ 514/540, 450

(56) References Cited

U.S. PATENT DOCUMENTS

| | | | |
|---|---|---|---|
| 4,740,432 A | * | 4/1988 | Bosserelle ................... 424/59 |
| 5,145,684 A | | 9/1992 | Liversidge et al. |
| 5,202,242 A | | 4/1993 | Mynderse et al. |
| 5,227,295 A | | 7/1993 | Baker |
| 5,362,634 A | | 11/1994 | Boeck et al. |
| 5,496,931 A | | 3/1996 | Boeck et al. |
| 5,539,089 A | | 7/1996 | Broughton et al. |
| 5,571,901 A | | 11/1996 | Boeck et al. |
| 5,591,606 A | | 1/1997 | Turner et al. |
| 5,631,155 A | | 5/1997 | Turner et al. |
| 5,670,364 A | | 9/1997 | Mynderse et al. |
| 5,670,486 A | | 9/1997 | Mynderse et al. |
| 5,767,253 A | | 6/1998 | Turner et al. |
| 5,840,861 A | | 11/1998 | Mynderse et al. |
| 6,001,981 A | | 12/1999 | DeAmicis et al. |
| 6,063,771 A | | 5/2000 | Snyder |
| 6,235,754 B1 | * | 5/2001 | Watson et al. ............... 514/315 |
| 6,342,482 B1 | * | 1/2002 | Snyder ......................... 514/31 |

FOREIGN PATENT DOCUMENTS

| | | |
|---|---|---|
| EP | 0 069 269 | 1/1983 |
| EP | 0 128 351 | 12/1984 |
| EP | 0 375 316 | 6/1990 |
| JP | 2837489 B2 | 11/1991 |
| JP | 03251520 | * 11/1991 |
| WO | WO 97/00265 | 1/1997 |
| WO | WO 97/33471 | 9/1997 |
| WO | WO 00/01347 | 6/1999 |
| WO | WO 00 29378 | 5/2000 |
| WO | WO 01/11963 | 8/2000 |
| WO | WO 00/60940 | 10/2000 |
| WO | WO 01/11961 | 2/2001 |
| WO | WO 01/11962 | 2/2001 |
| WO | WO 01/11964 | 2/2001 |
| WO | WO 01/12156 | 2/2001 |
| WO | WO 01/19840 | 3/2001 |
| WO | WO 01/40446 | 6/2001 |

OTHER PUBLICATIONS

Carl V. DeAmicis, et al., "Physical and Biological Properties of the Spinosyns: Novel Macrolide Pest–Control Agents from Fermentation," American Chemical Society, Chapter 11, pp. 144–154.

Spinosad Technical Guide.

Boech, et al., Chemical Abstracts, 114, 9, Abstract No. 80066m (1991).

Kirst, et al., "Discovery Isolation, and Structure Elucidation of a Family of Structurally Unique, Fermentation–Derived Tetracyclic Macrolides," ACS Symposium Series, Snythesis and Chemistry of Agrochemicals III, 504, pp. 214–225 (1992).

Crouse, et al., "Naturally Derived Materials as Products and Leads for Insect Control: The Spinosyns," Rev. Toxicol, 2, pp. 133–146 (1998).

Mertz, F. P., et al., "Saccharopolyspora spinosad sp. Nov. Isolated from Soil Collected in a Sugar Mill Rum Still," Int. J. System Bacteriol, 40, pp. 34–39 (1990).

Salgado, V. L., "Studies on the Mode of Action of Spinosad: Insect Symptoms and Physiological Correlates," Pestic. Biochem. Physiol., 60, pp. 91–102 (1998).

Thompson, G. D., et al., "Spinosad A Case Study: An Example from a Natural Products Discovery Programme," Pest. Manag. Sci., 56, pp. 696–702 (2000).

Thompson, G. D., "The Discovery of *Saccharopolyspora spinosad* and a New Class of Insect Control Products," Down to Earth, 52, pp. 1–5 (1997).

Breuninger, J. M., "Conserve SC: A New Product for the Turfgrass and Ornamental Industry," Down to Earth, 53, pp. 1–5 (1998).

Nolting, S. P., "Insect Control in Cotton with Tracer," Down to Earth, 52, pp. 21–27 (1997).

(Continued)

*Primary Examiner*—Alton Pryor
(74) *Attorney, Agent, or Firm*—John C. Demeter

(57) ABSTRACT

This invention provides topical ectoparasiticidal fomulations comprising an ectoparasiticide, preferably a pyrethroid or a spinosyn, a spreading agent at is a ($C_3$–$C_6$) branched alkyl ($C_{10}$–$C_{20}$) alkanoate, preferably isopropyl myristate, and optionally a miscibilizing agent compatible with organic solvent systems, and methods of controlling an ectoparasite infestation on certain animals comprising topically applying such formulations to the animal.

10 Claims, No Drawings

OTHER PUBLICATIONS

Sparks, et al., "Biological Activity of the Spinosyns, New Fermentation Derived Insect Control Agents, on Tobaco Budworm (Lepidopters: Noctuidae) Larvae," J. Econ. Entomol., 91, pp. 1277–1283 (1996).

Kirst, et al., Tetrahydron Letters, 32(37), 4839–4842 (1991).

Snyder, et al., J. Am. Chem. Soc., 106, 787–789 (1984).

T. C. Sparks, et al., "Biological Characteristics of the Spinosyns: A New Naturally Derived Insect Control Agents," Cotton Insect Research and Control Conference, 1995 Beltwide Cotton Conferences, pp. 903–907.

G. D. Thompson, "Spinosyns: An Overview of New Natural Insect Management Systems," Cotton Insect Research and Control Conference, 1995 Beltwide Cotton Conferences, pp. 1039–1043.

Database WPI, Week 198721, Derwent Publications Ltd., London, GB; AN 1987–145349; XP002153469 & HU 41 238 A (Nehezvegyipari), Apr. 28, 1987 abstract.

Chemical Abstracts, vol. 102, No. 3, Jan. 21, 1985 Columbus, Ohio, US; abstract No. 19640, Kieran, Peter John, et al: "Pour–on formulation for lice control" XP002153466 abstract & AU 83219 47 A (Wellcome Australia Ltd.) Apr. 12, 1984.

Chemical Abstractsm, vol. 101, No. 11, Sep. 10, 1984 Columbus, Ohio, US; abstract No. 85712, Kieran, Peter John, et al.: "Pyrethroids for combating sheep ectoparasites" XP002153467 abstract & AU 82918 50 A (Wellcome Australia Ltd.) Mar. 24, 1983.

Chemical Abstracts, vol. 100, No. 7, Feb. 12, 1984 Columbus, Ohio, US; abstract No. 47094, Kiernan, Peter John et al.: "Control of sheep lice" XP002153468 abstract & AU 81770 04 A (Wellcome Australia Ltd.) May 27, 1982.

*Agricultural Chemical News*, 195(2), "NAF–85 (spinosad): Dow–Elanco insecticide" (1995).

*Agricultural Chemical News*, 186(2), "Spinosad, NAF–144; DowElanco seeks EPA approval for insecticide" (1995).

Spencer, et al., "Spinosad insect control agent; lack of effects in a one year neurotoxicity screening study in rats," *Fundam. Appl. Tocicol.*; Pt. 2, 211, 30(1) (1996).

Kirst, et al., "Chemistry of Biology of the spinosyns a new class of naturally derived insect control agents," *Abstracts of Papers Americal Chemical Society: 210th American Chemical Society*, 210, Part 1, Abstract No. AGRO061.

Adan, et al., "Laboratory evaluation of the novel naturally derived compound spinosad against ceratitis capitata," *Pesticide Science*, 48(3), pp. 261–268 (1996).

Boyd, Impact of insecticides on predators of the soybean looper, pseudoplusia inc, *PhD Dissertation*, The Louisiana State University and Agricultural and Mechanical Col., UMI(9637762).

King, et al., Spinosad bait for the Caribbean fruit fly (Kiptera: Tephritidea), *Florida Entomologist*, 79(4) pp. 526–531 (1996); ISSN: 0015–4040.

Magnussen, et al., "Characterization of spinosad related residues in poultry tissues and eggs following oral administration," 211th *American Chemical Society National Meeting*, New Orleans, Louisiana, USA, 211:1–2; AGRO 43; ISSN 0065-7 (1996).

Saunders, et al., "Degradation of spinosad in aqueous solution," 211th *Americal Chemical Society National Meeting*, New Orleans, Louisiana, USA, 211, Part 1, Abstract No. AGRO048.

Sparks, et al., "Chemistry and biology of the spinosyns: components of spinosad (Tracer), the first entry into Dow-Elanco's naturalyte class of insect control products," *Proc.—Beltwide Cotton Conf.*, 2:692–696 (1996); ISSN: 1059–2644.

Burton, et al., "Tracer naturalyte insect control physical property attributes," *Proc.—Beltwide Cotton Conf.*, 2:696–697 (1996); ISSN: 1059–2644.

Thompson, et al., "Spinosad and the new naturalyte insect control class," *Proc.—Beltwide Cotton Conf.*, 2:870–872 (1996); ISSN: 1059–2644.

Murray, et al., "The effects of spinosad (Tracer) on pests and beneficials," *Australian Cottongrower*, 18:62–64 (1997).

Heller, et al., "Evaluation of experimental DowElanco NAF85 and NAF127 formulations, and Dursban Pro for management of black cutworm on creeping bentgrass, 1996," *Anthropod Management Tests*, 22:345 (1997).

Heller, et al., "Evaluation of NAF formulations, Dursban Pro, and Scimitar CS for management of black cutworm on creeping bentgrass, 1995," Arthropod Management Tests, 22:346 (1997).

Salgado, et al., "Studies on the mode of action of spinosad, the active ingredient in Tracer insect control," *Proc.—Beltwide Cotton Conference*, 2:1082–1084 (1997); ISSN: 1059–2644.

Murrey, et al., "The effect of spinosad (Tracer) on arthropod pest and beneficial populations in Australian cotton," *Proc.—Beltwide Cotton Conf.*, 2:1087–1091 (1997); ISSN: 1059–2644.

Sparks, et al., "Penetration and metabolism of spinosyn A in lepidopterous larvae," *Proc. —Beltwide Cotton Conference*, 2:1259–1264 (1997); ISSN: 1059–2644.

*Agriculture Chemical News*, "Success (spinosad): a new DowElanco insecticide formulation," 209: pp. 2–15 (1997).

*Agriculture Chemical News*, "Tracer (spinosad): DowElanco gains insecticide registration," 211; pp. 3–15 (1997).

*Agriculture Chemical News*, "Success (spinosad): Dow-Elacno gains 24(c) insecticide label to use in California," 213; pp. 2–15 (1997).

*Agriculture Chemical News*, "Conserve SC (spinosad): DowElanco gains EPA, USA, insecticide registration," 215; pp. 1–15 (1997).

Yeh, et al., "Application of empore disc extraction for trace analysis of spinosad and metabolites in leafy vegetables, pepper, and tomatoes by high–performance liquid chromatography with ultraviolet detection," *Journal of Agricultural and Food Chemistry*, vol. 45, No. 5, pp. 1746–1751; ISSN 0021–8561.

Boyd, et al., "Residual toxicity of selected insecticides to heteropteran predaceous species (Heteroptera: Lygaeidae, Nabidae, Pentatomidae) on soybean," *Environ. Entomol.*, vol. 27, No. 1, pp. 154–160 (1998).

Kolarid, et al., "Colorado potato beetle control, 1997," *Arthropod Management Tests*, vol. 23; pp. 124–126 (1998).

Cowles, "Effect of spinosad formulations and other miticides on twospotted spider mite, 1995," *Arthopod Management Tests*, vol. 23; pp. 342–343 (1998).

Kjaer, et al., "The impact of phenology, exposure and instar susceptibility on indecticide effects on a chrysomelid beetle population," *Prestic. Sci.*, vol. 52, No. 4, pp. 361–371 (1998).

Marty, et al., "The maternal and developmental toxicity of spinosad in Sprague–dawley rats and New Zealand White Rabbits," *Teratology*, vol. 57, pp. 4–5 (1998).

Salgado, et al., "Studies on the mode of action of spinosad: The internal effective concentration dependence of neural excitation," *Pesticide Biochemistry and Physiology*, vol. 60, No. 2, pp. 103–110 (1998).

Boyd, et al., "Susceptibility of predaceous hemipteran species to selected insecticides on soybean in Louisiana," *Journal of Economic Entomology*, vol. 91, No. 2, pp. 401–409 (1998).

Woodburn, et al., "Bioconcentration and metabolism of a unique inseticide (spinosyn) by the Rainbow trout," *Second World Congress of the Society of environmental toxicology and chemi*, PT127; pp. 5–9 (1995).

Stoltz, et al., "Colorado potato beetle control with foliar sprays, 1995," *Arthropod Management Tests*, vol. 21, pp. 168–169.

Sewell, et al., "Irish potato, control of Colorado potato beetle, 1995," *Arthropod Management Tests*, vol. 21, pp. 158–159.

Olson, et al., "Potato, Colorado potato beetle control with spinosad, 1995," *Arthropod Management Tests*, vol. 21; pp. 154–155.

Noetzel, et al., "Control of resistant Colorado potato beetle, Blaine, MN, 1995," *Arthropod Management Tests*, vol. 21, p. 149.

Noetzel, et al., "Colorado potato beetle control, Crookston, MN, 1995," *Arthropod Management Tests*, vol. 21, pp. 145–146.

Hedin, et al., "Physical and biological properties of the spinosyns: novel macrolide pest–control agents from fermentation," Phytochemicals for Pest Control, Chapter 11, 1995 *International Chemical Congress of Pacific Basin Societies*; ACS Symposium Series 658, pp. 144–153.

Boyd, "Impact of insecticides on predators of the soybean looper, Pseudoplusia inc, "*Dissertation*; UMI(9637762): [97pp]; The Lousiana State University and Agriculture.

Sears, et al., "Effects of various rates and combinations of insecticides on the control of Colorado potato beetle (CPB)(1995)," *Pest Management Research Report—Insects and Diseases*, ICAR: 86100104; pp. 159–161; Report No. 061 (1995).

J. M. Edwards, et al., "Potential of Spinosad as a Control Agent for Diptera," ESA Annual Meeting, Las Vegas, Nevada, Dec. 17–21 (1995).

* cited by examiner

TOPICAL ORGANIC ECTOPARASITICIDAL FORMULATIONS

This application is the National Stage of International Application No. PCT/US00/19549, filed Jul. 26, 2000, which claims the benefit of U.S. Provisional Application No. 60/148,508, filed Aug. 12, 1999.

This invention relates to topical organic ectoparasiticidal formulations. Ectoparasites such as fleas, blowflies, lice, ticks and mites can seriously affect productivity in the domesticated animal industries. Further, such parasites cause disease and discomfort for pets and other companion animals. Ectoparasites are often controlled by topically applying an insecticide or mixture of insecticides onto the animal. Topical ectoparasite control agents are usually applied in liquid formulations. The formulations can be applied by spot-on application, plunge or spray dipping, jetting with a hand held spray or in a race, or as a back-line spray or pour-on.

A particular problem with topical formulations is poor migration from the site of application. In the sheep industry, for example, treatment for ectoparasites is commonly carried out in the early season within 24 hours after shearing, or, less frequently, later in the season when the wool is longer. Especially with early season treatments, when the topical formulation is applied along the dorsal midline or back-line of the animal, the insecticide component of currently available commercial formulations migrates very poorly from the application site. Typically less than 10% of the applied insecticide diffuses away from the application site within the first 10 days. Thus, extensive areas of the animal's skin and/or hair may receive sublethal concentrations of the insecticide. These areas remain susceptible to damaging invasion by ectoparasites.

To overcome the inadequate control caused by poor migration of the insecticide, it has become common in the industry to apply relatively large amounts of insecticide. This practice introduces unwelcome costs, results in the presence of insecticide residues in certain animal products (such as wool and wool byproducts) and increases the potential of environmental pollution. It also increases the risk of unwanted and unnecessary exposure to pesticides to animal handlers and farmers treating the animals.

Solvent-based formulations have received attention in recent times in the search for greater insecticide mobility that would allow the same insecticidal effect to be achieved with less insecticide in the formulations. Up to the present, there has been little success in identifying a solvent that materially enhances the spread of insecticides that are applied using a spot-on or pour-on method.

This invention provides insecticidal formulations that can be applied topically to animals and that have the advantage of permitting the active ingredient to spread over the surface of the skin and/or hair of the treated animal, thereby providing more extensive coverage of the insecticide. These formulations, therefore, provide greater inhibition or eradication of ectoparasites with smaller amounts of insecticide.

The topical ectoparasiticidal formulations of this invention comprise an ectoparasiticide, a spreading agent and optionally a miscibilizing agent. More specifically, the invention relates to a topical ectoparasiticidal formulation comprising from about 0.1 to about 25 weight percent of an ectoparasiticide, from about 25 to about 99.9 weight percent of a ($C_3$–$C_6$) branched alkyl ($C_{10}$–$C_{20}$) alkanoate spreading agent, and optionally up to about 70 weight percent of a miscibilizing agent compatible with organic solvent systems.

An exemplary topical ectoparasiticidal formulation of this invention is one wherein the ectoparasiticide is a spinosyn, or a physiologically acceptable derivative or salt thereof.

This invention also encompasses a method of controlling an ectoparasite infestation on a small ruminant or companion animal, comprising topically applying to the hair and/or skin of the animal a formulation comprising from about 0.1 to about 25 weight percent of a spinosyn, or a physiologically acceptable derivative or salt thereof, from about 25 to 99.9 weight percent isopropyl myristate, and from 0 to about 70 weight percent of a miscibilizing agent compatible with organic solvent systems.

The invention also relates to an article of manufacture, comprising packaging material and a topical formulation for controlling an ectoparasite infestation on a small ruminant or companion animal contained within said packaging material, wherein said formulation comprises a topical unit dose of a formulation comprising 0.1 to about 25 weight percent of an ectoparasiticide, from about 25 to about 99.9 weight percent of a ($C_3$–$C_6$) branched alkyl ($C_{10}$–$C_{20}$) alkanoate spreading agent, and optionally up to about 70 weight percent of a miscibilizing agent compatible with organic solvent systems; and, wherein said packaging material comprises a label or package insert with instructions for topically administering the dose to the animal.

This article of manufacture or kit is particularly appropriate when the companion animal is a dog or a cat. The timing of administering the doses will generally be every 30 days. Each kit typically contains a sufficient number of doses to control the ectoparasite infestation for a period of several months.

This invention further provides a topical formulation for controlling an ectoparasite infestation on a small ruminant or companion animal comprising a spinosyn, or a derivative or salt thereof, and a spreading agent substantially as hereinbefore described with references to any one of the Examples.

Examples of small ruminant animals are a sheep, a goat or a camellid.

The term "companion animal" includes dogs, cats, horses and other pets owned and maintained in close association with humans as part of the human-animal bond.

The term "controlling" as used herein refers to either ameliorating or eliminating a current infestation or preventing an infestation in a susceptible host.

Many insecticidal agents are useful in the formulations of this invention. Indeed, any ectoparasiticidal compound that is soluble in a ($C_3$–$C_6$) branched alkyl ($C_{10}$–$C_{20}$) alkanoate vehicle and is useful for topical application can be incorporated as the insecticidal component of these formulations. Typically, the insecticidal agent is active against a broad spectrum of pest species, including acaricides, antiparasitic agents, insect growth regulators and compounds that inhibit or kill flies, flying pests and other "temporary" pests that only alight momentarily on domesticated animals.

Examples of useful classes of insecticides are spinosyns, organophospates, organochlorines, carbamates, and pyrethrins. Specific useful insecticidal compounds include tetraethyl pyrophosphate (TEPP), mevinphos, disulfoton, azinphosmethyl, parathion, methylparathion, chlorfenvinphos, cichlorvos, diazinon, dimethoate, trichlorfon, chlorothion, malathion, ronnel, abate, baygon, carbaryl, mobam, temik, zectran, methoxychlor, aldrin, dieldrin, endrin, heptachlor, chlordane, lindane, mirex, nicotine, rotenoids, pyrethrums, spinosyns and synthetic pyrethroids, including cypermethrin.

Preferred insecticides useful in these formulations are spinosyns or a pyrethroid such as cypermethrin. Spinosyns are especially preferred.

The spinosyns (also known as A83453 factors) are agricultural insecticides that have shown activity against southern armyworm and other insects in the order *Lepidoptera*, and cotton aphid and other members of the order *Homoptera*. (See, for example, U.S. Pat. No. 5,571,901).

The spinosyns were also known to have some ectoparasiticidal-activity, i.e., they had in vitro activity against mosquito larvae, black blowfly larvae and adult stable flies, which are members of the insect order *Diptera,* and transient systemic activity against larval blowfly and adult stable fly in guinea pigs and sheep. For these tests, the spinosyns were administered in aqueous polyvinylpyrrolidone or in polyethylene glycol (see U.S. Pat. No. 5,571,901, col. 26–32).

The spinosyns are naturally-derived macrolides produced by fermentation of *Saccharopolyspora spinosa.* The fermentation produces multiple factors, including spinosyn A and spinosyn D (also called A83543A and A8354D). Spinosyn A and spinosyn D are the two spinosyns that are most active as insecticides. An agricultural product comprised mainly of these two spinosyns is available commercially under the name "spinosad".

Spinosyn A was the first spinosyn isolated and identified from the fermentation broth of *Saccharopolyspora spinosa.* Subsequent examination of the fermentation broth revealed that *S. spinosa* produced a number of spinosyns that have been called spinosyns A to H and J. Additional spinosyns, denominated K to W, have been identified from various strains of *S. spinosa.* The various spinosyns are characterized by differences in the substitution patterns on the amino group of the forosamine, at selected sites on the tetracyclic ring system and on the 2N,3N,4N-(tri-O-methyl)rhamnose group.

Boeck et al. described spinosyns A–H and J (which they called A83543 factors A, B, C, D, E, F, G, H and J), and salts thereof, in U.S. Pat. No. 5,362,634 (issued Nov. 8, 1994); U.S. Pat. No. 5,496,932 (issued Mar. 5, 1996); and U.S. Pat. No. 5,571,901 (issued Nov. 5, 1996). Mynderse et al. described spinosyns L–N (which they called A83543 factors L, M and N), their N-dimethyl derivatives, and salts thereof, in U.S. Pat. No. 5,202,242 (issued Apr. 13, 1993); and Turner et al. described spinosyns Q–T (which they called A83543 factors Q, R, S and T), their N-dimethyl derivatives, and salts thereof, in U.S. Pat. No. 5,591,606 (issued Jan. 7, 1997) and U.S. Pat. No. 5,631,155 (issued May 29, 1997). Spinosyns K, O, P, U, V, W and Y are described, for example, by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation", pages 146–154 (1997).

The spinosyns can be isolated in the form of salts that are also useful in the formulations of this invention. The salts are prepared using standard procedures for salt preparation. For example, spinosyn A can be neutralized with an appropriate acid to form an acid addition salt. Representative suitable acid addition salts include salts formed by reaction with either an organic or inorganic acid, for example, sulfuric, hydrochloric, phosphoric, acetic, succinic, citric, lactic, maleic, funaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

The term a "spinosyn or a derivative thereof" as used herein refers to an individual spinosyn factor (spinosyn A, B, C, D, E, F, G, H, J, K, L, M, N, O, P, Q, R, S, T, U, V, W or Y), an N-dimethyl derivative of one or more spinosyn factor, or a combination thereof. For convenience, the term "spinosyn component" as used means an individual spinosyn or a physiologically acceptable derivative or salt thereof, or a combination thereof "Spinosad" as used herein refers to a mixture of spinosyns comprised mainly of spinosyns A and D.

The spinosyns are known to have excellent human and animal safety and toxicological profiles. Because of their low toxicity to animals and humans, spinosyns are considered to be environment-friendly, "green" insecticides. It is desirable to formulate spinosyns to maintain this "green" profile.

Spinosyns have recently been found to be useful in the eradication or control of ectoparasites on sheep and companion animals. Thus, formulations of spinosyns with low toxicity and increased stability are potentially valuable in combating ectoparasites and the diseases such pests often carry.

The present formulations further comprise a ($C_3$–$C_6$) branched alkyl ($C_{10}$–$C_{20}$) alkanoate. This component is an organic solvent that acts as a spreading agent. Spreading agents increase the spreading of, and aid in substantially equalizing the distribution of, the active ingredient over the hair and/or skin surface area of the animal over time. The spreading agent solvent system should be safe, non-toxic, environment-friendly and non-flammable.

The branched alkyl portion of the ($C_3$–$C_6$) branched alkyl ($C_{10}$–$C_{20}$) alkanoate includes all branched chain isomers of $C_3$–$C_6$ alkyl groups. Examples are isopropyl, isobutyl, isopentyl, and isohexyl. The ($C_{10}$–$C_{20}$) alkanoate moiety includes all $C_{10}$–$C_{20}$ fatty alkanoate groups, including but not limited to, decanoate ($C_{10}$), hendecanoate ($C_{11}$), dodecanoate ($C_{12}$), tridecanoate ($C_{13}$), tetradecanoate ($C_{14}$), pentadecanoate ($C_{15}$), hexadecanoate ($C_{16}$), heptadecanoate ($C_{17}$), octadecanoate ($C_{18}$), and eicosanoate ($C_{20}$). Preferably, the spreading agent is a ($C_3$–$C_6$) branched alkyl ($C_{12}$–$C_{16}$) alkanoate. Of these solvents, $C_3$- branched alkyl-$C_{14}$ alkanoates are especially useful. A preferred spreading agent is isopropyl myristate (IPM).

The formulations can optionally contain a miscibilizing agent. The miscibilizing agent aids in solubilizing the active ingredient and must be compatible with organic solvent systems. The phrase "compatible with organic solvent systems" means that the miscibilizing agent does not form more than one phase when mixed with the ($C_3$–$C_6$) branched alkyl ($C_{10}$–$C_{20}$) alkanoate component.

Suitable miscibilizing agents for use in these formulations generally are ($C_1$–$C_{30}$) organic acids. Typically, such organic acids are straight-chain saturated fatty acids, but they can also be low molecular weight organic acids such as formic acid, acetic acid, propionic acid and benzoic acid.

The choice of miscibilizing agent will vary depending on the insecticide in the formulation. When the insecticide component is a spinosyn, examples of suitable miscibilizing agents are formic acid, acetic acid, propionic acid, butyric acid, valeric acid, caproic acid, benzoic acid, enanthic acid, caprylic acid, pelargonic acid, capric acid, undecylic acid, lauric acid, tridecylic acid, myristic acid, pentadecylic acid, palmitic acid, margaric acid, stearic acid, oleic, arachidic acid, behenic acid, lignoceric acid, cerotic acid, montanic acid, triacontanoic acid, psyllic acid, and ceroplastic acid. Other useful miscibilizing agents are ($C_1$–$C_{30}$) alkyl sulfuric acids, ($C_1$–$C_{30}$) alky phosphoric acids, and ($C_1$–$C_{30}$) alkyl sulfonic acids.

In formulations containing a spinosyn solubilized in isopropyl myristate, for example, oleic acid is a particularly useful miscibilizing agent because it aids in solubilizing the spinosyn (thus allowing for the formation of solvent solutions containing relatively high concentrations of active ingredient), and it is compatible with the isopropyl myristate component.

Compounds other than ($C_1$–$C_{30}$) organic acids can also be useful miscibilizing agents in the formulations of this invention. In general, a miscibilizing compound useful for these formulations: 1) is compatible with the selected organic solvent component, and 2) solubilizes the active ingredient without substantially altering the spreading properties of the formulation.

When insecticide is a spinosyn and the spinosyn component is spinosyn D or spinosad (i.e., a mixture of spinosyns A and D), it is especially important that the miscibilizing agent is able to solubilize the spinosyn D sufficiently. In technical grade spinosad, factor D is generally the factor that causes solubility problems when preparing spinosad-containing formulations. Examples of miscibilizing agents that are useful for spinosad-containing ectoparasiticidal formulations of the present invention include, but are not limited to, benzyl alcohol, ethylene glycol phenyl ether, D-limonene, N-methyl-2-pyrrolidinone, and methylated soybean oils and soybean oil methyl esters, such as SOY-GOLD 1000 (AG Environmental Products LLC).

The present formulations can also contain other optional ingredients, such as: antioxidants, UV-absorbing compounds or photostabilizers, viscosity-modifying agents, antimicrobial agents, dyes, perfumes, deodorants and physiologically or dermatological acceptable carriers, diluents, excipients or adjuvants. Such agents are known in the art.

For example, one or more antioxidants can be added to the formulations in an amount effective to retard oxidation of the formulation components and the ensuing degradative effects. Potentially useful antioxidants include primary antioxidants that are radical scavengers, such as hindered phenolics and secondary amines, and secondary antioxidants, such as phosphites and thioesters that function as peroxide decomposers. Preferred antioxidants for use in these formulations are blends of primary and secondary antioxidants, including particularly blends of phenolic and phosphite antioxidant compositions.

There are many commercially available antioxidants products designed for polymer stabilization, including antioxidant formulations comprising synergistic combinations of primary and secondary antioxidants. Examples of commercially available antioxidants useful in the formulations of this invention include the Irganox® antioxidants available from Ciba Geigy, Vanox® antioxidants from R. T. Vanderbilt, and the Naugard® antioxidants available from Uniroyal Chemicals.

When the formulations include an antimicrobial component, it should be present in an amount effective to prevent the growth of microorganisms in the formulation.

Generally, the formulations of this invention can be prepared by blending the components with adequate mixing or stirring. For example, a useful spinosad formulation is one having a final concentration of 2 mg of spinosad per mL. One such formulation is prepared to contain 99.1 weight percent IPM, 0.6 weight percent oleic acid, and 0.3 weight percent spinosad technical (89% active ingredient). This formulation is made by adding the appropriate amount of spinosad to the IPM solvent with mixing or stirring, blending the oleic acid into the IPM/spinosad mixture, and continuing the mixing or stirring until the spinosad has completely solubilized to form the final formulation product. An optional additional step is to filter the final formulation to remove any impurities or extraneous materials.

The formulations of this invention are applied to the animal topically. Topical control protocols include spot-on or pour-on treatments wherein the formulation is placed directly onto a discreet skin and/or hair surface area of the animal and allowed to spread over the remainder of the animal's skin or hair surface area. Generally, spot-on or pour-on protocols involve initially placing the formulation on the dorsal midline (i.e., the head, neck, shoulders or back) of the animal. Placement typically occurs on a dorsal midline surface area that constitutes less than 10% of the animal's entire surface area For example, a typical pour-on treatment protocol involves applying about 4 to about 50 mL of a liquid ectoparasiticidal formulation in a narrow strip along the backline of an animal, from the withers to the tail or rump.

For spot-on or pour-on treatment to control ectoparasites, such as lice, which are present over the whole surface of an animal, the ectoparasiticidal active ingredient must spread from the narrow strip at the backline to cover the entire surface of the animal. The present formulations have this advantageous spreading effect. Of course, they can be applied to areas of skin that constitute greater than 10% of the surface area of the animal, but such applications limit the advantage offered by these formulations. Another advantage of these formulations is that they offer extended ectoparasiticidal coverage and need not be applied more than weekly or biweekly at most.

EXAMPLE 1

Wetting Tests for Various Solvent Systems

To determine organic solvents that are useful spreading agents, solvent systems that are capable of solubilizing at least 1% spinosad by weight percent were screened for hair wetting by applying about 1 mL of the solvent system (solvents were screened without active ingredient), dropwise, to a tanned rabbit pelt that was at an angle of about 45°. Solvent systems that wet the rabbit hair and did not run off before wetting the hair were considered to pass the screen. Table I describes the ability of selected organic solvents to wet the rabbit hair.

TABLE I

Ability of Solvents and Aqueous Surfactant Systems to Wet Rabbit Hair on Tanned Rabbit Pelts.

| Organic Solvent | |
| --- | --- |
| Wet Well | Did Not Wet |
| isopropyl myristate | triacetin |
| methyl laurate | N-methyl pyrrolidone |
| dipropylene glycol methyl ether | propylene glycol |
| butyl lactate | |
| methyl caprate | |
| methyl oleate | |
| octanoic acid | |
| limonene | |
| hexanol | |
| ethyl oleate | |

As Table I shows, water immiscible, nonpolar solvents generally wet well, although dipropylene glycol methyl ether is water miscible and did wet the hair very well.

EXAMPLE 2

Formulation Spreading Tests

Further studies were conducted to determine the abilities of various solvents to aid in spreading of active ingredient.

International Patent Application WO 9524219 teaches that wool grease fraction (F1) provides superior spreading of pyrethroid insecticides on sheep when compared to organic solvent spreading agents. Tests were conducted to compare the spreading properties of formulations containing the F1 wool grease faction and various organic solvents. The amount and rate of diffusion of $^{14}$C-labeled zeta-cypermethrin from the dorsal midline of sheep were determined when applied in F1 wool grease fraction and a range of test excipients. Four formulations containing 10 mg/mL zeta-cypermethrin spiked with 100 $\mu$Ci [$^{14}$C] zeta-cypermethrin were prepared in the following vehicles: wool grease fraction F1, isopropyl myristate, octyl stearate and glyceryl tricaprylate/caprate. A dose of 1 mL/5 kg body weight of each formulation was applied to the backline of 3 sheep. Wool was collected and pooled 1, 2, 4, 8, 11 and 14 days after treatment from three 12×12 mm squares chosen at random, along meridian lines drawn 2, 7.5 and 15 cm down the side of each sheep from the backline. The clipped areas were also swabbed. At day 14 after treatment the wool at the site of application was collected, and back and perirenal fat samples were collected. The quantity of zeta-cypermethrin in each sample was measured by liquid scintillation counting.

For the majority of the measurements taken, isopropyl myristate gave the greatest spread of zeta-cypermethrin and the wool grease fraction F1 provided the least spreading. When the vehicle was the F1 wool grease fraction, only the 2-cm meridian showed increased concentration of zeta-cypermethrin over time after initial application. When the vehicle was isopropyl myristate, the quantity of zeta-cypermethrin measured at all meridians increased with time following administration. Octyl stearate and glyceryl tricaprylate/caprate gave modest spread, but not as great as the spread provided by the IPM formulations. Tissue residues were similar amongst formulations except the glyceryl tricaprylate/caprate formulation appeared to cause the highest residue levels.

After two weeks it was determined that F1 was a comparatively poor spreading agent, octyl stearate and glyceryl tricaprylate/caprate provided better spreading properties, and isopropyl myristate gave the best spread of zeta-cypermethrin.

EXAMPLE 3
Ectoparasiticidal Efficacy Tests of Wool Grease and IPM Formulations

Tests were conducted to compare the efficacy of formulations of spinosad in F1 wool grease fraction versus those in isopropyl myristate against lice on sheep. Two F1 formulations containing spinosad at 2 mg/mL and 10 mg/mL, and one formulation containing 2 mg/mL spinosad in isopropyl myristate were made as follows:

a) F1 Formulation (2 mg/mL)
   81.11% F1
   18.62% solvent (50/50 petroleum ether/acetone)
   0.27% spinosad technical that was 89% active
   100% (w/w)
   Formulation density=0.84 g/mL
b) F1 Formulation (10 mg/mL)
   80.26% F1
   18.42% solvent (50/50 petroleum ether/acetone)
   1.32% spinosad technical that was 89% active 100%
   Formulation density=0.84 g/mL
c) IPM Formulation (2 mg/mL)
   99.123% IPM
   0.613% oleic acid
   0.264% spinosad technical that was 89% active 100%
   Formulation density=0.85 g/mL Each formulation was administered to sheep as a pour-on application immediately after shearing. Spinosad/F1 formulations were tested at doses of 0 (i.e., vehicle alone), 0.4 and 2 mg/kg, while the spinosad/IPM formulation was tested at a dose of 0.4 mg/kg. The 2 mg/kg dose of spinosad/F1 was administered using the 10 mg/mL formulation, while the 0.4 mg/kg doses were administered using the 2 mg/mL formulations. Lice counts were taken on the sheep at sites all over the animal, including the head and neck. These lice counts were taken before treatment and on or about weekly for the following eight weeks. The results of this study are summarized in Table II.

TABLE II

Comparison of Ectoparasiticidal Efficacy of Spinosad in F1 and IPM Formulations in Sheep Lice Counts (mean)

| | Day 0 lice count | Week of Study | | | | | | | |
|---|---|---|---|---|---|---|---|---|---|
| | | 1 | 2 | 3 | 4 | 5 | 6 | 7 | 8 |
| F1 Only | 643 | 428 | 328 | 350 | 237 | 245 | 159 | 156 | 145 |
| 0.4 mg/kg Spinosad/F1 | 622 | 391 | 213 | 211 | 159 | 118 | 103 | 69 | 68 |
| 2 mg/kg Spinosad/F1 | 582 | 146 | 86 | 48 | 2 | 13 | 4 | 3 | 2 |
| 0.4 mg/kg Spinosad/IPM | 575 | 138 | 81 | 68 | 47 | 32 | 13 | 25 | 21 |

As the results summarized in Table II show, spinosad in IPM at a dose of 0.4 mg/kg was superior in lice control to spinosad in F1 at 0.4 mg/kg, and was almost equal in efficacy to spinosad in F1 at 2 mg/kg. Spinosad in IPM gave outstanding control of lice on sheep, including control of lice on the head and neck, which indicated that IPM potentiated the spreading of spinosad from the dorsal midline to the head, neck and other body surface regions:

EXAMPLE 4
Efficacy of Spinosad in Various Organic Solvents vs. Lice in Sheep

Further lice efficacy studies on sheep were conducted to compare the efficacy of IPM as a spreading agent to that of other organic solvent systems containing blends of organic solvents. The formulations tested had the following compositions:

a) IPM Formulation:
  99.12% IPM
  0.61% oleic acid
  0.27% spinosad technical (89% active)
b) OP/IPM Formulation
  79.78% octyl palmitate (OP)
  19.95% IPM
  0.27% spinosad technical (89% active)
c) GTCC/OP Formulation
  79.78% glyceryl tricaprylate/caprate (GTCC)
  19.95% octyl palmitate
  0.27% spinosad technical (89% active)
d) GTCC/IPM/CAP Formulation
  69.81% glyceryl tricaprylate/caprate
  14.96% IPM
  14.96% cetearyl octanoate (CAP)
  0.27% spinosad technical (89% active)
e) OP/IPM/OSU Formulation
  69.81% octyl palmitate
  14.96% IPM
  14.96% dioctyl succinate (OSU)
  0.27% spinosad technical (89% active)
f) TPM/LWG/GTCC Formulation
  59.84% tripropylene glycol methyl ether (TPM)
  19.95% liquid wool grease (LWG)
  19.95% glyceryl tricaprylate/caprate
  0.27% spinosad technical (89% active)
g) TPM/OSU Formulation
  79.78% tripropylene glycol methyl ether
  19.95% dioctyl succinate
  0.27% spinosad technical (89% active)

Lice counts were taken on the sheep at sites all over the animal, including the head and neck. These lice counts were taken before treatment and on or about weekly for the following twelve weeks. The results of this study summarized in Table III.

TABLE III

Efficacy of Spinosad in Organic Solvent Formulations vs. Lice in Sheep
Lice Count (mean)

| Treatment | Pre-treatment lice count | Weeks | | | | | |
|---|---|---|---|---|---|---|---|
| | | 1 | 2 | 4 | 6 | 8 | 12 |
| Control | 253 | 197 | 128 | 163 | 206 | 162 | 204 |
| IPM | 268 | 33 | 23 | 18 | 20 | 18 | 18 |
| OP/IPM | 271 | 71 | 51 | 83 | 90 | 71 | 184 |
| GTCC/OP | 257 | 32 | 28 | 40 | 52 | 46 | 106 |
| GTCC/IPM/CAP | 278 | 28 | 16 | 24 | 25 | 22 | 33 |
| OP/TPM/OSU | 259 | 33 | 19 | 23 | 22 | 19 | 40 |
| TM/LWG/GTCC | 267 | 53 | 29 | 39 | 34 | 27 | 48 |
| TPM/OSU | 259 | 58 | 38 | 64 | 62 | 66 | 119 |

As Table III shows, spinosad in IPM alone was the most effective treatment of the 7 formulations tested. A strong correlation exists between the results of the spreading experiments and those of the field efficacy experiments. Spinosad formulations in IPM exhibited excellent spreading characteristics and demonstrated outstanding long-term protective and inhibitory effects against ectoparasiticidal infestation in sheep.

Examples 5–11 illustrate various formulations of this invention.

EXAMPLE 5

Spinosad/IPM/Acetic Acid Formulation 5.65% spinosad (88.5% active)
3% acetic acid
91.35% IPM

EXAMPLE 6

Spinosad/IPM/Octanoic Acid Formulation 5.65% spinosad (88.5% active)
7.5% octanoic acid
86.85% IPM

EXAMPLE 7

Spinosad/IPM/Lauric Acid Formulation 5.65% spinosad (88.5% active)
10.15% lauric acid
84.2% IPM

EXAMPLE 8

Spinosad/IPM/Oleic Acid Formulation 5.65% spinosad (88.5% active)
16.5% oleic acid
77.85% IPM

EXAMPLE 9

Spinosad/IPM/Benzoic Acid Formulation 5.65% spinosad (88.5% active)
3.76% benzoic acid
90.59% IPM

EXAMPLE 10

Spinosad/IPM/NMP Formulation 5.65% spinosad (88.5% active)
40.0% 1-methyl-2-pyrrolidinone (NMP)
54.35% IPM

EXAMPLE 11

Zeta-Cypermethrin/IPM Formulation 1.18% zeta-cypermethrin (84.7% active)
98.82% IPM The formulations of Examples 5–10 can be prepared by weighing the spinosad into a suitable container, adding the IPM and stirring to create a slurry, and then adding the final component and stirring until a clear solution is achieved. In preparing the formulation of Example 11, the zeta-cypermethrin is an oily liquid that requires gentle heating (approximately 40–50° C.) to allow for proper mixing into the organic solvent phase. No separation of phases is evident upon cooling.

What is claimed is:

1. A topical ectoparasiticidal formulation comprising from 0.1 to 25 weight percent of a spinosyn, or a physiologically acceptable derivative or salt thereof; from 25 to 99 weight percent of isopropyl myristate and from 0.6 to 40 weight percent of a miscibilizing agent compatible with organic solvent systems, wherein the miscibilzing agent is selected from acetic, lauric, octanoic, oleic and benzoic acids and N-methyl-2-pyrrolidinone wherein the formulation is spot-on or pour-on.

2. A topical ectoparasiticidal formulation comprising: from about 0.1 to about 25 weight percent of an ectoparasiticide, selected from a spinosyn, or a physiologically acceptable derivative or salt thereof; from about 25 to about 99.9 weight percent of a $(C_3-C_6)$ branched alkyl $(C_{10}-C_{20})$ alkanoate spreading agent; and from about 0.6 to about 40 weight percent of a miscibilizing agent compatible with organic solvent systems wherein the miscibilizing agent is selected from formic, acetic, propionic, benzoic, butyric, valeric, caproic, enanthic, caprylic, pelargonic, capric, undecylic, lauric, tridecylic, myristic, pentadecylic, palmitic, margaric, stearic, olcic, arachidic, behenic, lignoceric, cerotic, montanic, triacontanoic, psyllic, or ceroplastic acids, or benzyl alcohol, ethylene glycol phenyl ether, D-limonene N-methyl-2-pyrrolidinone, methylated soybean oils and soybean oil methyl esters; wherein the formulation is spot-on or pour-on.

3. A formulation of claim 2 wherein the spreading agent is a $(C_3-C_6)$ branched alkyl $(C_{12}-C_{16})$ alkanoate.

4. A formulation of claim 3 wherein the $(C_3-C_6)$ branched alkyl $(C_{12}-C_{16})$ alkanoate is isopropyl myristate.

5. A formulation of claim 2, 3 or 4 which further comprises an effective amount of an antimicrobial agent.

6. An article of manufacture, comprising packaging material and contained within said packaging material a topical formulation for controlling an ectoparasite infestation on a small ruminant or companion animal, wherein said formulation comprises a topical unit dose of a formulation of claim 2, 3 or 4; and, wherein said packaging material comprises a label or package insert with instructions for topically administering the dose to the animal.

7. A method of controlling an ectoparasite infestation on a small ruminant or companion animal, comprising topically applying to the hair and/or skin of the animal a formulation of claim 2, 3 or 4.

8. A formulation of claim 2, 3 or 4 wherein the miscibilizing agent is oleic acid.

9. An article of manufacture, comprising packaging material and contained within said packaging material a topical formulation for controlling an ectoparasite infestation on a small ruminant or companion animal, wherein said formulation comprises a topical unit dose of a formulation of claim 1 or 8; and, wherein said packaging material comprises a label or package insert with instructions for topically administering the dose to the animal.

10. A method of controlling an ectoparasite infestation on a small ruminant or companion animal, comprising topically applying to the animal a formulation of claim 1 or 8 by a spot-on or pour-on protocol.

* * * * *